US012163946B2

(12) United States Patent
Kasahara et al.

(10) Patent No.: US 12,163,946 B2
(45) Date of Patent: Dec. 10, 2024

(54) CONCRETE STRUCTURE DETERIORATION DETERMINATION METHOD, DEVICE AND PROGRAM

(71) Applicant: NIPPON TELEGRAPH AND TELEPHONE CORPORATION, Tokyo (JP)

(72) Inventors: Hisatoshi Kasahara, Tokyo (JP); Yosuke Takeuchi, Tokyo (JP); Yosuke Okamura, Tokyo (JP); Junichiro Tamamatsu, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 183 days.

(21) Appl. No.: 17/913,150

(22) PCT Filed: Mar. 26, 2020

(86) PCT No.: PCT/JP2020/013772
§ 371 (c)(1),
(2) Date: Sep. 20, 2022

(87) PCT Pub. No.: WO2021/192169
PCT Pub. Date: Sep. 30, 2021

(65) Prior Publication Data
US 2023/0375524 A1 Nov. 23, 2023

(51) Int. Cl.
*G01N 33/38* (2006.01)
(52) U.S. Cl.
CPC .................. *G01N 33/383* (2013.01)
(58) Field of Classification Search
CPC .............................. G01N 17/00; G01N 33/383
(Continued)

(56) References Cited

U.S. PATENT DOCUMENTS 5,426,973 A * 6/1995 Hartt .................... G01N 33/383
73/762
7,181,978 B2 * 2/2007 Shtakelberg .......... G01N 33/383
73/803

(Continued)

FOREIGN PATENT DOCUMENTS

JP 2015121470 A 7/2015
JP 2017198463 A 11/2017

OTHER PUBLICATIONS

"Methods of test for chloride ion content in hardened concrete" (2011) JIS A 1154: 2011 [online] Accessed on: Feb. 5, 2020, website: https://kikakurui.com/a1/A1154-2012-01.html.

(Continued)

Primary Examiner — Andre J Allen (57) ABSTRACT

An assessment device (1) according to the present disclosure includes a determination unit (10) that determines a first period corresponding to a shortest period until deterioration of a concrete structure due to an aging-induced deterioration cause appears and a second period shorter than the first period and corresponding to a longest period until deterioration of the concrete structure due to a material-induced deterioration cause appears and an assessment unit (20) that assesses that a deterioration causing material is used in a concrete structure having, in a checking result indicating a period elapsed from construction of the concrete structure and the presence or absence of deterioration in the concrete structure, the deterioration and the period elapsed from the construction which is not shorter than the second period and is shorter than the first period.

18 Claims, 8 Drawing Sheets

(58) Field of Classification Search
USPC .................................................. 73/760–803
See application file for complete search history.

(56) References Cited

U.S. PATENT DOCUMENTS

| | | | | |
|---|---|---|---|---|
| 7,225,682 B2* | 6/2007 | Shtakelberg | ......... | G01N 33/383 |
| | | | | 73/803 |
| 7,987,728 B2* | 8/2011 | Song | ................... | G01M 5/0033 |
| | | | | 73/803 |
| 12,013,331 B2* | 6/2024 | Fujimoto | ............. | G01N 33/383 |
| 2013/0131999 A1* | 5/2013 | Hussain | ................. | G01N 17/00 |
| | | | | 702/32 |
| 2023/0258621 A1* | 8/2023 | Noguchi | ............. | G01N 33/383 |
| | | | | 73/803 |

OTHER PUBLICATIONS

"Method of test for alkali-silica reactivity of aggregates by chemical method" (2017) JIS A 1145: 2017 [online] Accessed on: Feb. 5, 2020, website: http://kikakurui.com/a1/A1145-2017-01.html.

* cited by examiner

| DETERIORATION CAUSE | CAUSE-SPECIFIC SHORTEST PERIOD | CAUSE-SPECIFIC LONGEST PERIOD |
|---|---|---|
| DETERIORATION CAUSE A (AGING) | $\alpha$ | — |
| DETERIORATION CAUSE B (AGING) | $\beta$ | — |
| DETERIORATION CAUSE C (MATERIAL) | — | $\gamma$ |
| DETERIORATION CAUSE D (MATERIAL) | — | $\delta$ |

Fig. 3

| CONSTRUCTION YEAR (PERIOD ELAPSED FROM CONSTRUCTION) | STRUCTURE NAME | PRESENCE/ABSENCE OF DETERIORATION |
|---|---|---|
| 1972 (x 1 YEAR) | STRUCTURE 1 | ABSENT |
| 1973 (x 2 YEARS) | STRUCTURE 2 | PRESENT |
| 1974 (x 3 YEARS) | STRUCTURE 3 | PRESENT |
| 197- (x 4 YEARS) | STRUCTURE 4 | ABSENT |
| 197- (x 5 YEARS) | STRUCTURE 5 | PRESENT |
| 198- (x 6 YEARS) | STRUCTURE 6 | ABSENT |
| 1983 (x 7 YEARS) | STRUCTURE 7 | PRESENT |
| 1984 (x 8 YEARS) | STRUCTURE 8 | PRESENT |
| 1985 (x 9 YEARS) | STRUCTURE 9 | PRESENT |
| 198- (x 10 YEARS) | STRUCTURE 10 | ABSENT |
| 199- (x 11 YEARS) | STRUCTURE 11 | PRESENT |
| 199- (x 12 YEARS) | STRUCTURE 12 | ABSENT |
| 20-- (x 13 YEARS) | STRUCTURE 13 | PRESENT |
| 2001 (x 14 YEARS) | STRUCTURE 14 | ABSENT |
| 2002 (x 15 YEARS) | STRUCTURE 15 | ABSENT |
| PRESENT TIME (YEAR IN WHICH CHECKING IS PERFORMED) | | |

| CONSTRUCTION YEAR (PERIOD ELAPSED FROM CONSTRUCTION) | STRUCTURE NAME | PRESENCE/ ABSENCE OF DETERIORATION | |
|---|---|---|---|
| 1972 (x 1 YEAR) | STRUCTURE 1 | ABSENT | FIRST GENERATION |
| 1973 (x 2 YEARS) | STRUCTURE 2 | PRESENT | |
| 1974 (x 3 YEARS) | STRUCTURE 3 | PRESENT | |
| 197- (x 4 YEARS) | STRUCTURE 4 | ABSENT | |
| 197- (x 5 YEARS) | STRUCTURE 5 | PRESENT | |
| 198- (x 6 YEARS) | STRUCTURE 6 | ABSENT | SECOND GENERATION |
| 1983 (x 7 YEARS) | STRUCTURE 7 | PRESENT | |
| 1984 (x 8 YEARS) | STRUCTURE 8 | PRESENT | |
| 1985 (x 9 YEARS) | STRUCTURE 9 | PRESENT | |
| 198- (x 10 YEARS) | STRUCTURE 10 | ABSENT | |
| 199- (x 11 YEARS) | STRUCTURE 11 | PRESENT | THIRD GENERATION |
| 199- (x 12 YEARS) | STRUCTURE 12 | ABSENT | |
| 20-- (x 13 YEARS) | STRUCTURE 13 | PRESENT | |
| 2001 (x 14 YEARS) | STRUCTURE 14 | ABSENT | |
| 2002 (x 15 YEARS) | STRUCTURE 15 | ABSENT | |
| PRESENT TIME (YEAR IN WHICH CHECKING IS PERFORMED) | | | |

$\beta$ line separates first and second generation.
$\gamma$ line separates second and third generation.

Fig. 8

| CONSTRUCTION YEAR (PERIOD ELAPSED FROM CONSTRUCTION) | STRUCTURE NAME | PRESENCE/ ABSENCE OF DETERIORATION | DETERIORATION CAUSING MATERIAL |
|---|---|---|---|
| 1972 (x 1 YEAR) | STRUCTURE 1 | ABSENT | ABSENT |
| 1973 (x 2 YEARS) | STRUCTURE 2 | PRESENT | UNKNOWN |
| 1974 (x 3 YEARS) | STRUCTURE 3 | PRESENT | UNKNOWN |
| 197- (x 4 YEARS) | STRUCTURE 4 | ABSENT | ABSENT |
| 197- (x 5 YEARS) | STRUCTURE 5 | PRESENT | UNKNOWN |
| 198- (x 6 YEARS) | STRUCTURE 6 | ABSENT | ABSENT |
| 1983 (x 7 YEARS) | STRUCTURE 7 | PRESENT | PRESENT |
| 1984 (x 8 YEARS) | STRUCTURE 8 | PRESENT | PRESENT |
| 1985 (x 9 YEARS) | STRUCTURE 9 | PRESENT | PRESENT |
| 198- (x 10 YEARS) | STRUCTURE 10 | ABSENT | ABSENT |
| 199- (x 11 YEARS) | STRUCTURE 11 | PRESENT | UNKNOWN |
| 199- (x 12 YEARS) | STRUCTURE 12 | ABSENT | UNKNOWN |
| 20-- (x 13 YEARS) | STRUCTURE 13 | PRESENT | UNKNOWN |
| 2001 (x 14 YEARS) | STRUCTURE 14 | ABSENT | UNKNOWN |
| 2002 (x 15 YEARS) | STRUCTURE 15 | ABSENT | UNKNOWN |
| PRESENT TIME (YEAR IN WHICH CHECKING IS PERFORMED) | | | |

CONCRETE STRUCTURE DETERIORATION DETERMINATION METHOD, DEVICE AND PROGRAM

CROSS-REFERENCE TO RELATED APPLICATIONS

This application is a U.S. National Stage Application filed under 35 U.S.C. § 371 claiming priority to International Patent Application No. PCT/JP2020/013772, filed on 26 Mar. 2020, the disclosure of which is hereby incorporated herein by reference in its entirety.

TECHNICAL FIELD

The present invention relates to an assessment method, an assessment device, and a program.

BACKGROUND ART

In recent years, appearance of a deterioration phenomenon such as cracking or exposure of a reinforcing steel bar in a concrete structure made of reinforced concrete has presented a social problem. When cracking occurs in reinforced concrete, an internal reinforcing steel bar is exposed directly to air to result in accelerated corrosion of the reinforcing steel bar, and consequently a bearing force of the structure rapidly decreases. Accordingly, it is important to accurately predict a time at which reinforced concrete undergoes deterioration such as cracking.

There are a plurality of causes of deterioration occurring in reinforced concrete, which are roughly categorized as causes of deterioration induced by aging even though a material used during construction does not particularly have a problem (hereinafter referred to as "aging-induced deterioration causes"), such as neutralization, and causes of deterioration induced by a material used during construction (hereinafter referred to as "material-induced deterioration causes").

In performing appropriate maintenance management on a concrete structure, deterioration prediction is used in most cases in which deterioration simulation/acceleration tests are performed by experiment, and a progress of deterioration is examined. However, to take sufficient use of knowledge obtained by the deterioration prediction, which deterioration cause induces a deterioration phenomenon in a concrete structure to be examined is required to be clear. In other words, it is necessary to preliminarily assess whether the concrete structure to be examined is a structure in which the aging-induced deterioration cause induces the deterioration phenomenon or a structure in which the material-induced deterioration cause induces the deterioration phenomenon. The deterioration prediction is a means for making a suggestion about an appropriate repair and maintenance method/timing and, when the concrete structure to be examined is the structure in which the material-induced deterioration cause induces the deterioration phenomenon, by specifying that the material-induced deterioration cause induces the deterioration phenomenon, a more appropriate repair and maintenance method can be suggested. In other words, by assessing whether or not a material (hereinafter referred to as the "deterioration causing material") serving as the deterioration cause is used in the concrete structure, it is possible to perform more efficient maintenance management of the concrete structure.

Examples of the deterioration cause due to a material included during construction include salt damage resulting from use of sea sand and cracking in concrete resulting from use of an aggregate that causes an alkali-silica-reaction (ASR). As a method of assessing the presence or absence of the deterioration causing material, there is a method that measures a concentration of salt in a specimen collected from a concrete structure, a method of observing an ASR rock type of the specimen collected from the concrete structure, or the like (see, e.g., Patent Literatures 1 and 2 and Non-Patent Literatures 1 and 2).

CITATION LIST

Patent Literature

[PTL 1] Japanese Patent Application Publication No. 2015-121470
[PTL 2] Japanese Patent Application Publication No. 2017-198463

Non-Patent Literature

[NPL 1] JIS A 1154, "Methods of test for chloride ion content in hardened concrete", [online], [Retrieved on Feb. 28, 2020]", Internet <URL: https://kikakurui.com/a1/A1154-2012-01.html>
[NPL 2] JIS A 1145: 2017, "Methods of test for alkali-silica reactivity of aggregates by chemical method", [online], [Retrieved on Feb. 28, 2020]", Internet <URL: http://kikakurui.com/a1/A1145-2017-01.html>

SUMMARY OF THE INVENTION

Technical Problem

In the method of colleting the specimen from the concrete structure described above, it is basically inevitable to destroy a portion of the concrete structure, which requires cost and time. There is also a concrete structure for which a bearing force reduced by a destructive test is undesirable. In addition, the number of concrete structures to be examined may be enormous, and even a non-destructive test may place a heavy load.

An object of the present disclosure achieved in view of problems as described above is to provide an assessment method, an assessment device, and a program which allow the presence or absence of a deterioration causing material used in a concrete structure to be non-destructively assessed and allow more efficient maintenance management of the concrete structure.

Means for Solving the Problem

To solve the problems described above, an assessment method according to the present disclosure is an assessment method that assesses the presence or absence of a deterioration causing material used in a concrete structure and causing deterioration therein, the method including: a determination step of determining a first period corresponding to a shortest period until deterioration of the concrete structure due to an aging-induced deterioration cause appears and a second period shorter than the first period and corresponding to a longest period until deterioration of the concrete structure due to a material-induced deterioration cause appears; and an assessment step of assessing that the deterioration causing material is used in a concrete structure having, in a checking result indicating a period elapsed from construction of the concrete structure and presence/absence of deterioration in the concrete structure, the deterioration and the period elapsed from the construction which is not shorter than the second period and is shorter than the first period.

To solve the problems described above, an assessment device according to the present disclosure is an assessment device that assesses the presence or absence of a deterioration causing material used in a concrete structure and causing deterioration therein, the device including: a determination unit that determines a first period corresponding to a shortest period until deterioration of the concrete structure due to an aging-induced deterioration cause appears and a second period shorter than the first period and corresponding to a longest period until deterioration of the concrete structure due to a material-induced deterioration cause appears; and an assessment unit that assesses that the deterioration causing material is used in a concrete structure having, in a checking result indicating a period elapsed from construction of the concrete structure and presence/absence of deterioration in the concrete structure, the deterioration and the period elapsed from the construction which is not shorter than the second period and is shorter than the first period.

To solve the problems described above, a program according to the present disclosure causes a computer to function as the assessment device described above.

Effects of the Invention

The assessment method, the assessment device, and the program according to the present disclosure allow the presence or absence of a deterioration causing material used in a concrete structure to be non-destructively assessed and allow more efficient maintenance management of the concrete structure.

DESCRIPTION OF EMBODIMENTS

A description will be given below of embodiments of the present disclosure with reference to the drawings.

Figure 1:
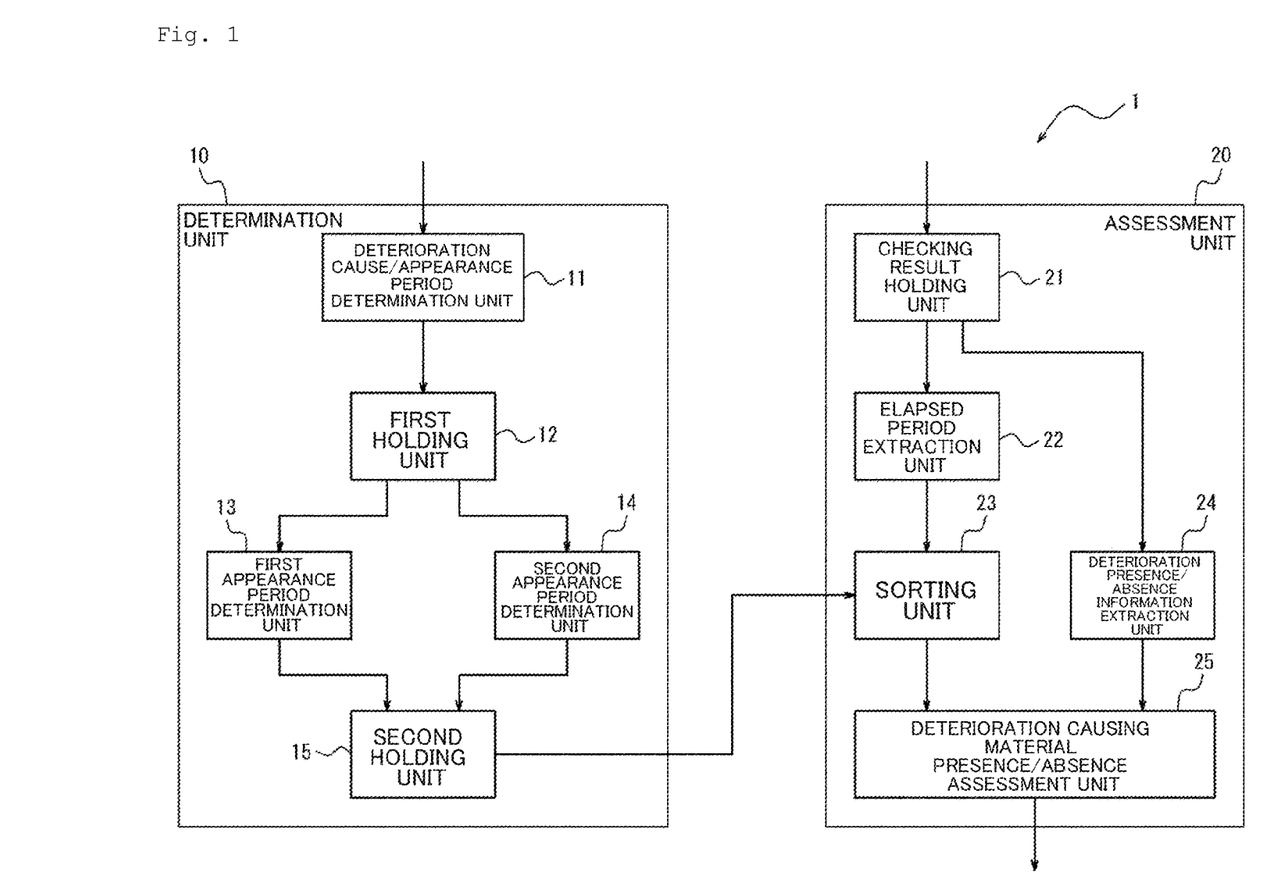
FIG. 1 is a diagram illustrating an example of a configuration of an assessment device according to an embodiment of the present disclosure.

FIG. 1 is a diagram illustrating a schematic configuration of an assessment device 1 according to one of the embodiments of the present disclosure. The assessment device 1 according to the present embodiment non-destructively assesses the presence or absence of a deterioration causing material used in a concrete structure made of reinforced concrete.

The assessment device 1 illustrated in FIG. 1 includes a determination unit 10 and an assessment unit 20.

The determination unit 10 determines a shortest period (first period) until appearance of aging-induced deterioration, which corresponds to a shortest period until deterioration (e.g., cracking) in the concrete structure due to an aging-induced deterioration cause appears. The determination unit 10 also determines a longest period (second period) until appearance of material-induced deterioration, which corresponds to a longest period until deterioration in the concrete structure due to a material-induced deterioration cause appears. In general, the deterioration due to the aging-induced deterioration cause is deterioration induced by entrance of a deterioration causing material from the outside. Meanwhile, the deterioration due to the material-induced deterioration cause is deterioration induced by a deterioration causing material present in the concrete. Accordingly, the shortest period until appearance of the aging-induced deterioration is longer than the longest period until appearance of the material-induced deterioration.

The determination unit 10 includes a deterioration cause/appearance period determination unit 11, a first holding unit 12, a first appearance period determination unit 13, a second appearance period determination unit 14, and a second holding unit 15.

The deterioration cause/appearance period determination unit 11 specifies a deterioration cause that deteriorates the concrete structure. The deterioration cause/appearance period determination unit 11 also determines whether the specified deterioration cause is the aging-induced deterioration cause or the material-induced deterioration cause. The deterioration cause/appearance period determination unit 11 also predicts a period until deterioration due to the specified deterioration cause appears (period until deterioration due to the deterioration cause appears after construction of the concrete structure).

A cause of deterioration that may occur in a concrete structure can be estimated from data on an environment (such as a latitude/longitude, a temperature, or a humidity) in which the concrete structure is present, a material (such as a type of aggregate or a type of cement) used in the concrete structure, a construction year, and the like. The deterioration cause/appearance period determination unit 11 receives an input of such data and predicts, based on the input data, the deterioration cause.

Known examples of the aging-induced deterioration cause include "neutralization" caused by carbon dioxide in air and "chemical erosion" caused by sulfate ions and the like contained in soil or the like. Meanwhile, known examples of the material-induced deterioration cause include "salt damage resulting from use of sea sand" and "cracking resulting from use of an ASR causing aggregate". The deterioration cause/appearance period determination unit 11 can determine, based on such knowledge, whether the specified deterioration cause is the aging-induced deterioration cause or the material-induced deterioration cause.

Next, the deterioration cause/appearance period determination unit 11 performs, for each of the deterioration causes, prediction (deterioration prediction) of a period until deterioration appears. Specifically, the deterioration cause/appearance period determination unit 11 predicts, for the aging-induced deterioration cause, a shortest period until the deterioration due to the deterioration cause appears (hereinafter referred to as the "cause-specific shortest period").

Meanwhile, the deterioration cause/appearance period determination unit 11 predicts, for the material-induced deterioration cause, a longest period until the deterioration due to the deterioration cause appears (hereinafter referred to as the "cause-specific longest period"). The deterioration cause/appearance period determination unit 11 can predict, based on, e.g., a prediction formula produced from a result of a test which simulates a material of a concrete structure to be examined, an environment in which the concrete structure is present, and the like, the periods until the deteriorations due to the deterioration causes appear. Alternatively, the deterioration cause/appearance period determination unit 11 may also predict, based on, e.g., a result of an investigation obtained from an existing literature or the like, the periods until the deteriorations due to the deterioration causes appear.

Note that, when there are a plurality of the concrete structures to be examined in a wide range, environments (such as temperatures and humidities) in which the individual concrete structures are present are different or materials (such as ratios of sea sand in use or water/cement ratios) of the concrete structures are different and, even though the deterioration cause is the same, the cause-specific shortest period or the cause-specific longest period predicted for each of the concrete structure may vary. In such a case, the deterioration cause/appearance period determination unit 11 predicts, for, e.g., the aging-induced deterioration cause, the shortest period until the deterioration due to the deterioration cause appears and predicts, for the material-induced deterioration cause, the longest period until the deterioration due to the deterioration cause appears.

It may also be possible that whether the cause of deterioration in the concrete structure is the aging-induced deterioration cause or the material-induced deterioration cause and the period until the deterioration due to either of the deterioration causes appears are determined in advance and input to the determination unit 10.

The deterioration cause/appearance period determination unit 11 outputs, to the first holding unit 12, whether the specified deterioration cause is the aging-induced deterioration cause or the material-induced deterioration cause and the period until the deterioration due to the deterioration cause appears (the cause-specific shortest period or the cause-specific longest period).

It is assumed hereinafter that there are deterioration causes A and B each serving as the aging-induced deterioration cause and there are deterioration causes C and D each serving as the material-induced deterioration cause. It is also assumed that the cause-specific shortest period of the deterioration cause A is $\alpha$, the cause-specific shortest period of the deterioration cause B is $\beta$ ($\beta<\alpha$), the cause-specific longest period of the deterioration cause C is $\gamma$ ($\gamma<\beta$), and the cause-specific longest period of the deterioration cause D is $\delta$ ($\delta<\gamma$).

Figure 2:
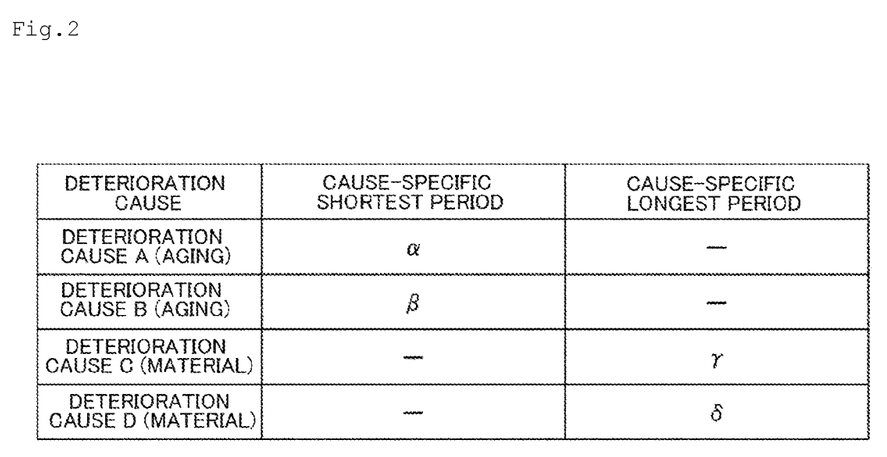
FIG. 2 is a diagram for illustrating deterioration causes and periods until appearance of deterioration which are stored in a first holding unit illustrated in FIG. 1.

The first holding unit 12 stores the deterioration cause, whether the deterioration cause is the aging-induced deterioration cause or the material-induced deterioration cause, and the period (the cause-specific shortest period or cause-specific longest period) until the deterioration due to the deterioration cause appears, each output from the deterioration cause/appearance period determination unit 11, in association with each other. Specifically, as illustrated in FIG. 2, the first holding unit 12 stores, for each of the deterioration causes, whether the deterioration cause is the aging-induced deterioration cause or the material-induced deterioration cause. In addition, the first holding unit 12 stores, for the aging-induced deterioration cause (each of the deterioration causes A and B), the cause-specific shortest period. Meanwhile, the first holding unit 12 stores, for the material-induced deterioration cause (each of the deterioration causes C and D), the cause-specific longest period.

Referring again to FIG. 1, the first appearance period determination unit 13 acquires the cause-specific shortest periods of the aging-induced deterioration causes, which are stored in the first holding unit 12. The first appearance period determination unit 13 determines the shortest one of the acquired cause-specific shortest periods to be the shortest period until appearance of the aging-induced deterioration and outputs the shortest period until appearance of the aging-induced deterioration to the second holding unit 15. In the example illustrated in FIG. 2, the first appearance period determination unit 13 determines the period $\beta$ to be the shortest period until appearance of the aging-induced deterioration.

The second appearance period determination unit 14 acquires the cause-specific longest periods of the material-induced deterioration causes, which are stored in the first holding unit 12. The second appearance period determination unit 14 determines the longest one of the acquired cause-specific longest periods to be the longest period until appearance of the material-induced deterioration and outputs the longest period until appearance of the material-induced deterioration to the second holding unit 15. In the example illustrated in FIG. 2, the second appearance period determination unit 14 determines the period $\gamma$ to be the longest period until appearance of the material-induced deterioration.

The second holding unit 15 stores the shortest period until appearance of the aging-induced deterioration, which is output from the first appearance period determination unit 13, and the longest period until appearance of the material-induced deterioration, which is output from the second appearance period determination unit 14.

The assessment unit 20 acquires a checking result indicating a period elapsed from construction of a concrete structure and the presence or absence of deterioration (e.g., cracking) in the concrete structure. The assessment unit 20 assesses that a deterioration causing material is used in a concrete structure having, in the checking result, deterioration and a period elapsed from construction which is not shorter than the longest period until appearance of the material-induced deterioration and is shorter than the shortest period until appearance of the aging-induced deterioration.

The assessment unit 20 includes a checking result holding unit 21, an elapsed period extraction unit 22, a sorting unit 23, a deterioration presence/absence information extraction unit 24, and a deterioration causing material presence/absence assessment unit 25.

To the checking result holding unit 21, the checking result of the concrete structure is input. The checking result is a result of checking the presence or absence of deterioration such as cracking in the concrete structure. Such checking is performed by a large number of companies or the like in management of the concrete structure. The checking result holding unit 21 stores the checking result input thereto.

Figure 3:
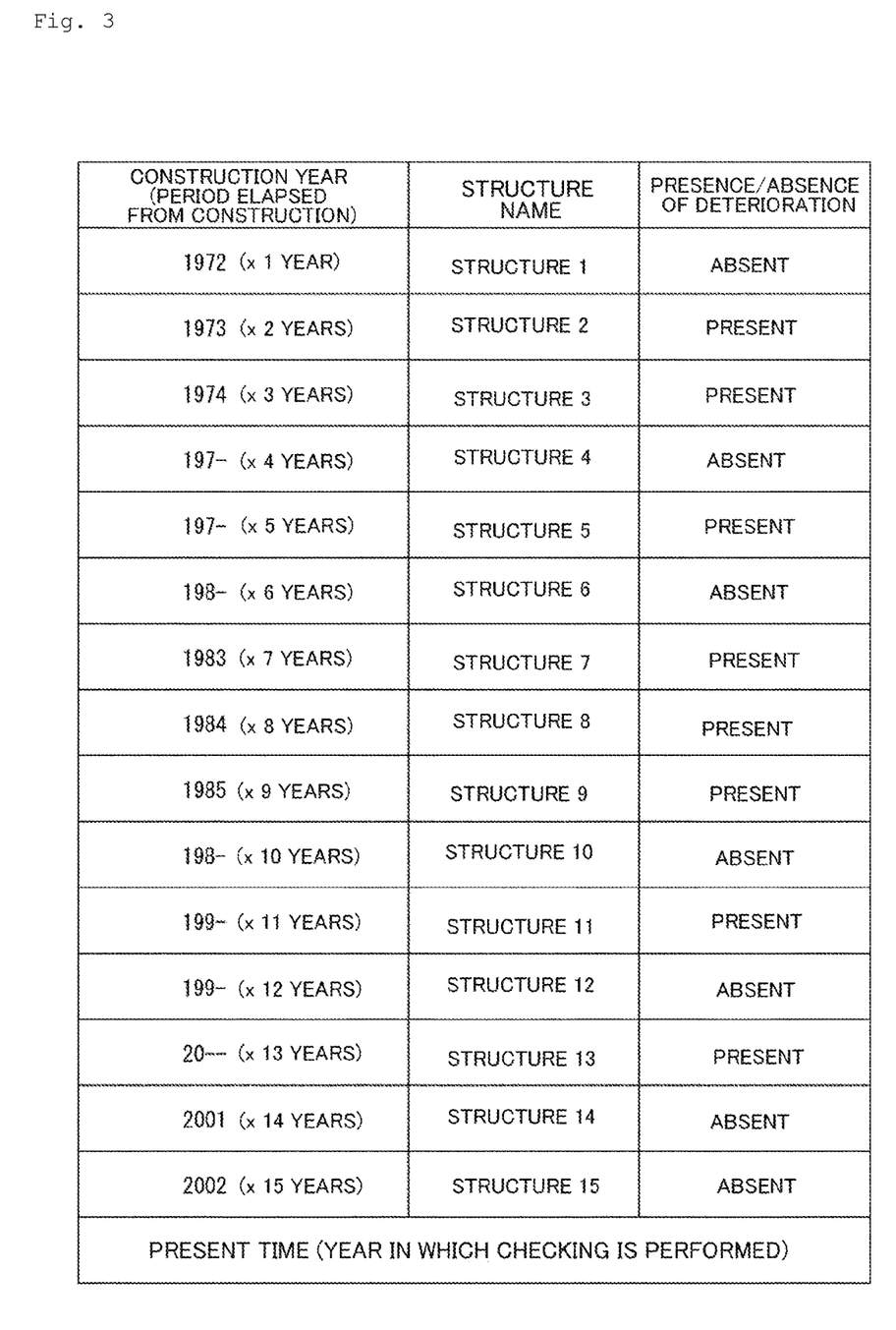
FIG. 3 is a diagram illustrating an example of a checking result stored in a checking result holding unit illustrated in FIG. 1.

As illustrated in, e.g., FIG. 3, the checking result holding unit 21 stores years of construction of concrete structures, names of the concrete structures, and deterioration presence/absence information indicating the presence or absence of deterioration (e.g., cracking) in association with each other. The checking result holding unit 21 may also store, together with the years of construction of the concrete structures or instead of the years of construction of the concrete structures, periods x elapsed from the construction of the concrete structures.

Referring again to FIG. 1, the elapsed period extraction unit 22 extracts, from the checking result stored in the checking result holding unit 21, the structure names of the concrete structures and the periods elapsed from the construction of the concrete structures, and outputs the structure names and the elapsed periods to the sorting unit 23.

The sorting unit 23 sorts, based on the periods elapsed from the construction of the individual concrete structures output from the elapsed period extraction unit 22, the individual concrete structures into three generations determined by the shortest period until appearance of the aging-induced deterioration and the longest period until appearance of the material-induced deterioration, which are stored in the second holding unit 15. Specifically, the sorting unit 23 sorts the individual concrete structures into the three generations, i.e., the generation (hereinafter referred to as the "first generation") the elapsed period from which is not shorter than the shortest period until appearance of the aging-induced deterioration, the generation (hereinafter referred to as the "second generation") the elapsed period from which is not shorter than the longest period until appearance of the material-induced deterioration and is shorter than the shortest period until appearance of the aging-induced deterioration, and the generation (hereinafter referred to as the "third generation") the elapsed period from which is shorter than the longest period until appearance of the material-induced deterioration. The sorting unit 23 outputs a result of the sorting to the deterioration causing material presence/absence assessment unit 25.

The deterioration presence/absence information extraction unit 24 extracts, from the checking result holding unit 21, the structure name of each of the concrete structures and the deterioration presence/absence information of the concrete structure, and outputs the structure name and the deterioration presence/absence information to the sorting unit 23.

The deterioration causing material presence/absence assessment unit 25 assesses, based on the deterioration presence/absence information output from the deterioration presence/absence information extraction unit 24, whether or not a deterioration causing material is used in each of the concrete structures sorted into the individual generations by the sorting unit 23, and outputs a result of the assessment. For example, the deterioration causing material presence/absence assessment unit 25 adds, to the checking result stored in the checking result holding unit 21, a result of assessing the presence or absence of a deterioration causing material in use and outputs the checking result with the assessment result.

Note that each of the determination unit 10 and the assessment unit 20 can be implemented by causing a processor mounted in a computer or the like to execute the program according to the present disclosure. As the processor, a versatile processor such as a CPU (Central Processing Unit) or a dedicated processor specific to specified processing can be used. The processor may also include one or more dedicated circuits. Alternatively, it may also be possible to replace the one or more processors with one or more dedicated circuits. As the dedicated circuit, e.g., a FPGA (Field-Programmable Gate Array) or an ASIC (Application Specific Integrated Circuit) can be used.

Next, a description will be given of an operation of the assessment device 1 according to the present embodiment.

Figure 4:
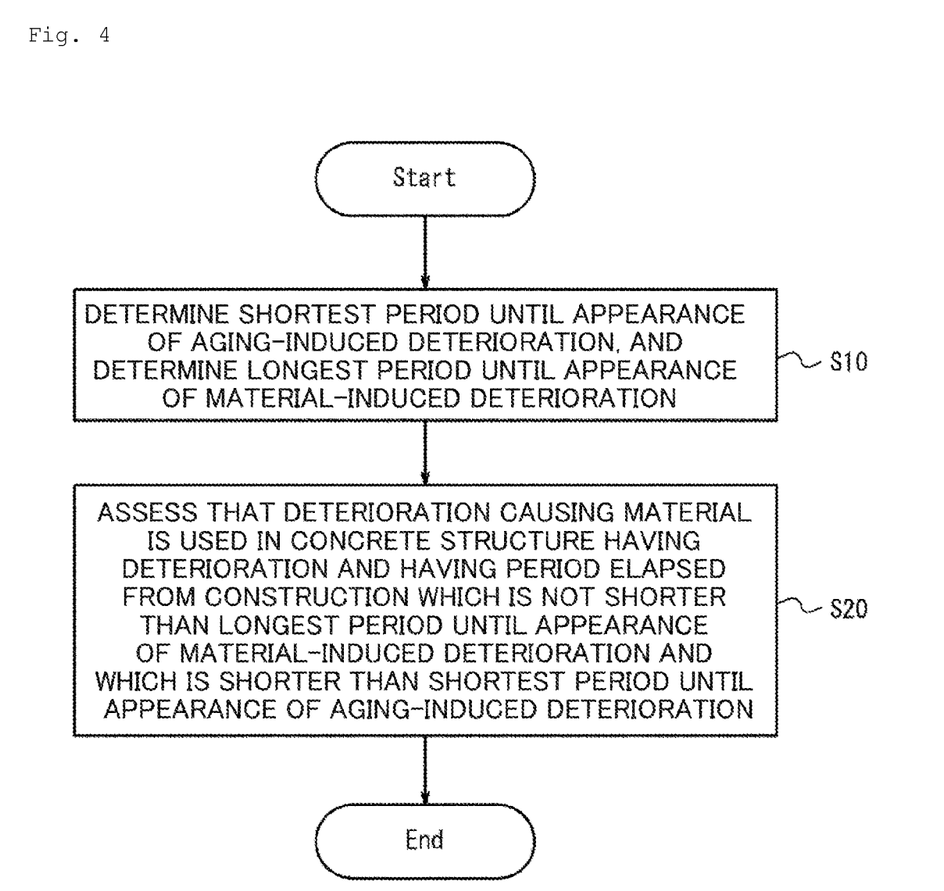
FIG. 4 is a flow chart illustrating an example of an operation of the assessment device illustrated in FIG. 1.

FIG. 4 is a flow chart illustrating an example of an operation of the assessment device 1 according to the present embodiment, which is a diagram for illustrating an assessment method according to the present embodiment.

The determination unit 10 determines the shortest period (first period) until appearance of the aging-induced deterioration and the longest period (second period) until appearance of the material-induced deterioration (Step S10).

The assessment unit 20 assesses that a deterioration causing material is used in a structure having, in the checking result, deterioration and the period x elapsed from the construction which is not shorter than the longest period (second period) until appearance of the material-induced deterioration and is less than the shortest period (first period) until appearance of the aging-induced deterioration (Step S20).

Thus, the assessment method according to the present embodiment includes a determination step (Step S10) of determining the shortest period (first period) until appearance of the aging-induced deterioration and the longest period (second period) until appearance of the material-induced deterioration and an assessment step (Step S20) of assessing that a deterioration causing material is used in the concrete structure having, in the checking result, deterioration and the period x elapsed from the construction which is not shorter than the longest period (second period) until appearance of the material-induced deterioration and is less than the shortest period (first period) until appearance of the aging-induced deterioration.

The following will describe processing in Step S10 (the determination step) and Step S20 (the assessment step) in greater detail. First, referring to FIG. 5, a more detailed description will be given of an operation in Step S10.

Figure 5:
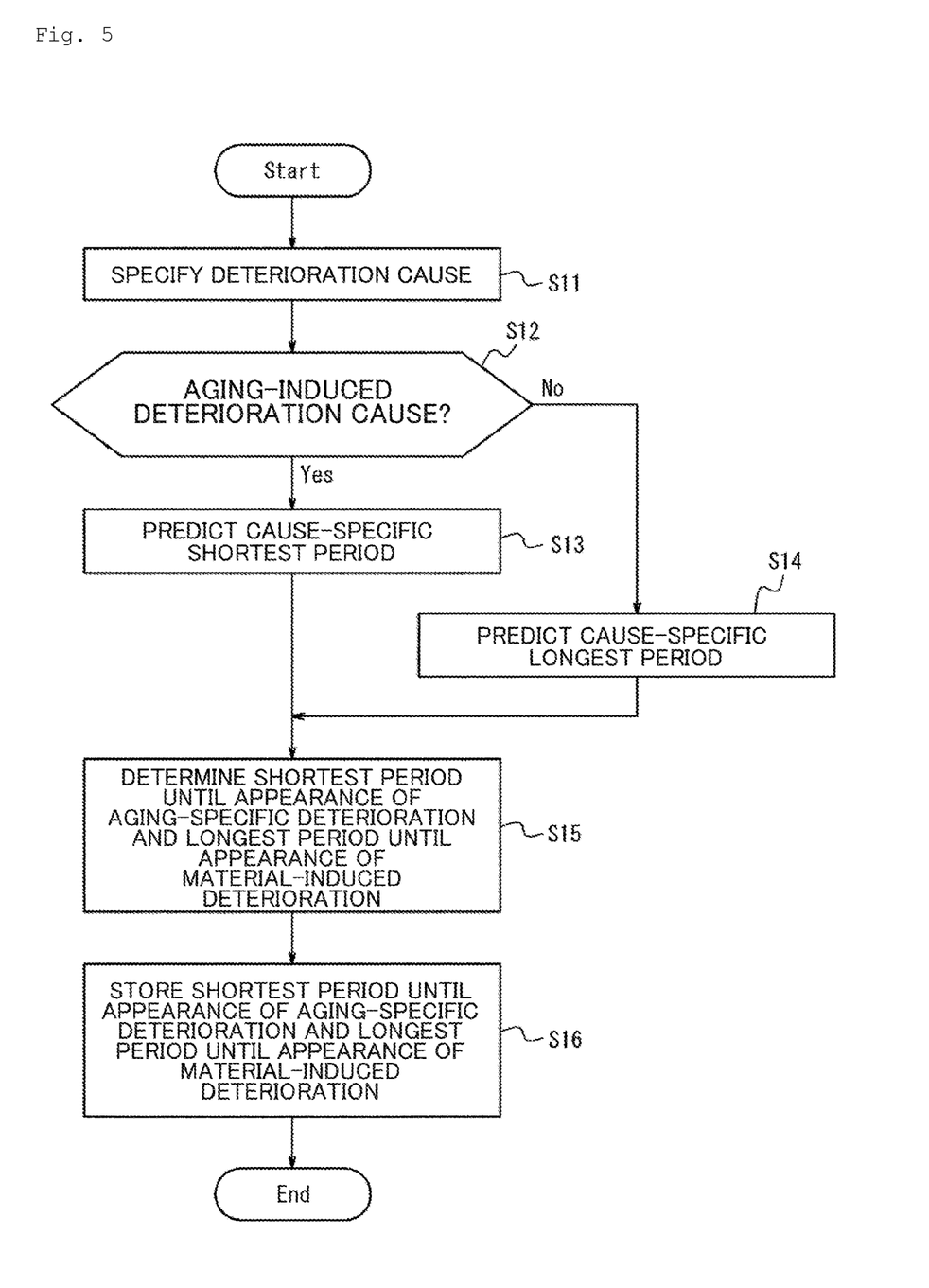
FIG. 5 is a flow chart illustrating processing in Step S10 illustrated in FIG. 4 in greater detail.

The deterioration cause/appearance period determination unit 11 specifies the deterioration cause based on the environment in which the concrete structure to be examined is present, the material used in the concrete structure, and the like (Step S11). It is assumed hereinafter that, as has been described with reference to FIG. 2, the deterioration causes A and B are specified as the aging-induced deterioration causes, and the deterioration causes C and D are specified as the material-induced deterioration causes.

The deterioration cause/appearance period determination unit 11 determines whether or not the specified deterioration causes are the aging-induced deterioration causes (Step S12).

When determining that the specified deterioration causes are the aging-induced deterioration causes (Yes in Step S12), the deterioration cause/appearance period determination unit 11 predicts the cause-specific shortest period of each of the deterioration causes (Step S13).

When determining that the specified deterioration causes are not the aging-induced deterioration causes (No in Step S12), i.e., when the specified deterioration causes are the material-induced deterioration causes, the deterioration cause/appearance period determination unit 11 predicts the cause-specific longest period of each of the deterioration causes (Step S14). The deterioration cause/appearance period determination unit 11 performs the processing in Steps S12 to S14 described above for each of the specified deterioration causes.

It is assumed hereinafter that, as has been described with reference to FIG. 2, the cause-specific shortest period of the aging-induced deterioration cause A is $\alpha$. It is also assumed that the cause-specific shortest period of the aging-induced deterioration cause B is $\beta$ ($\beta<\alpha$). It is also assumed that the cause-specific longest period of the material-induced deterioration cause C is $\gamma$ ($\gamma<\beta$). It is also assumed that the cause-specific longest period of the material-induced deterioration cause D is $\delta$ ($\delta<\gamma$).

The deterioration causes and the predicted cause-specific shortest periods/cause-specific longest periods are stored in the first holding unit 12.

The first appearance period determination unit 13 acquires the cause-specific shortest periods of the aging-induced deterioration causes stored in the first holding unit 12. The first appearance period determination unit 13 determines the shortest one of the acquired cause-specific shortest periods to be the shortest period until appearance of the aging-induced deterioration. The second appearance period determination unit 14 acquires the cause-specific longest periods of the material-induced deterioration causes stored in the first holding unit 12. The second appearance period determination unit 14 determines the longest one of the acquired cause-specific longest periods to be the longest period until appearance of the material-induced deterioration (Step S15). In the example described above, the first appearance period determination unit 13 determines the cause-specific shortest period $\beta$ of the deterioration cause B to be the shortest period until appearance of the aging-induced deterioration (which may be hereinafter referred to as the "shortest period $\beta$ until appearance of the aging-induced deterioration"). Meanwhile, the second appearance period determination unit 14 determines the cause-specific longest period $\gamma$ of the deterioration cause C to be the longest period until appearance of the material-induced deterioration (which may be hereinafter referred to as the "longest period $\gamma$ until appearance of the material-induced deterioration").

Thus, in the determination step, for each of the plurality of aging-induced deterioration causes, the period until the deterioration of the concrete structure due to the deterioration cause appears is predicted. Then, of the periods predicted for the plurality of aging-induced deterioration causes, the shortest period is determined to be the shortest period (first period) until appearance of the aging-induced deterioration. Also, in the determination step, for each of the plurality of material-induced deterioration causes, the period until the deterioration of the concrete structure due to the deterioration cause appears is predicted. Then, of the periods predicted for the plurality of material-induced deterioration causes, the longest period is determined to be the longest period (second period) until appearance of the material-induced deterioration.

The second holding unit 15 stores the shortest period until appearance of the aging-induced deterioration, which is determined by the first appearance period determination unit 13, and the longest period until appearance of the material-induced deterioration, which is determined by the second appearance period determination unit 14 (Step S16).

Figure 6:
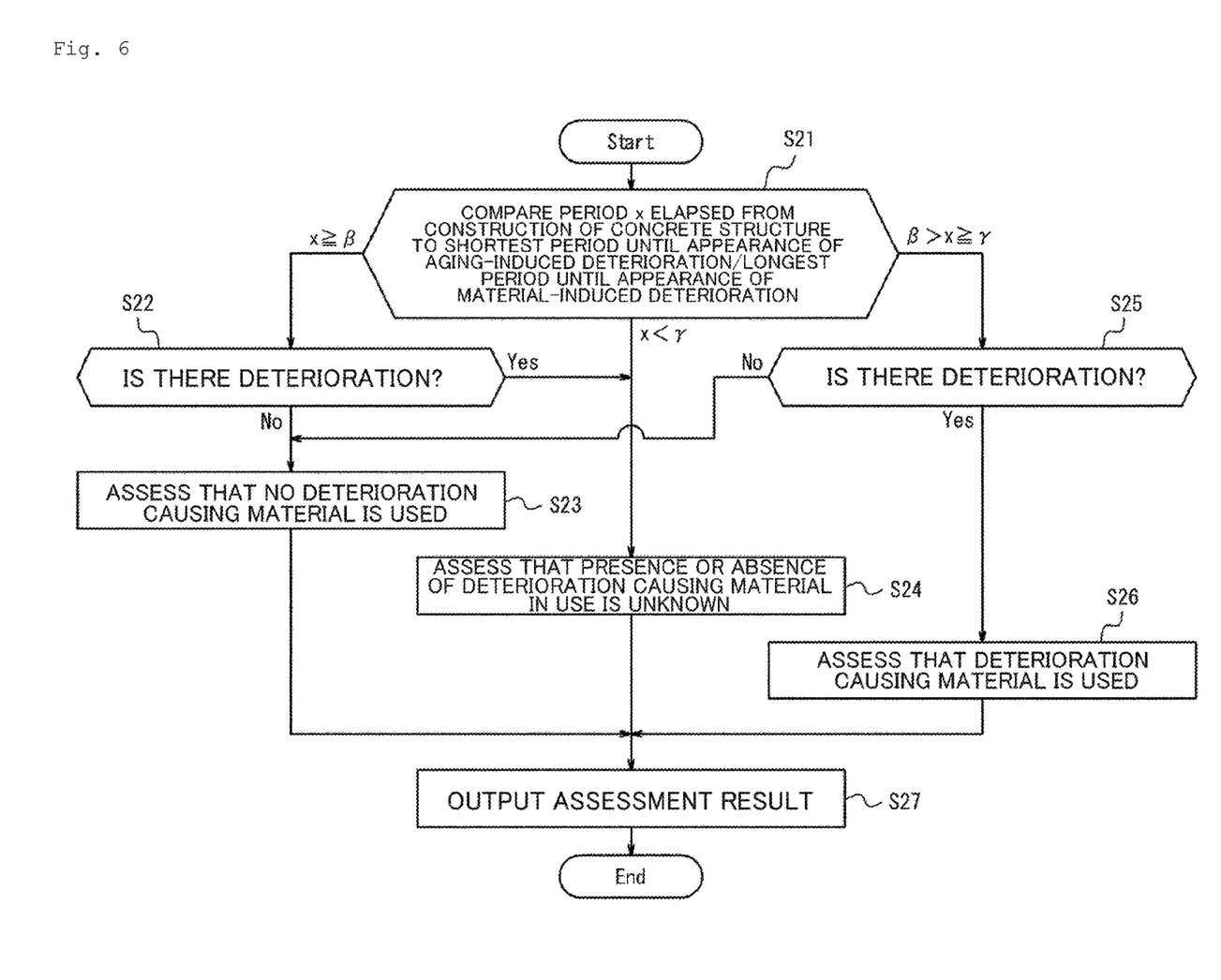
FIG. 6 is a flow chart illustrating processing in Step S20 illustrated in FIG. 4 in greater detail.

Next, referring to FIG. 6, a more detailed description will be given of processing in Step S20 (assessment step).

Figure 7:
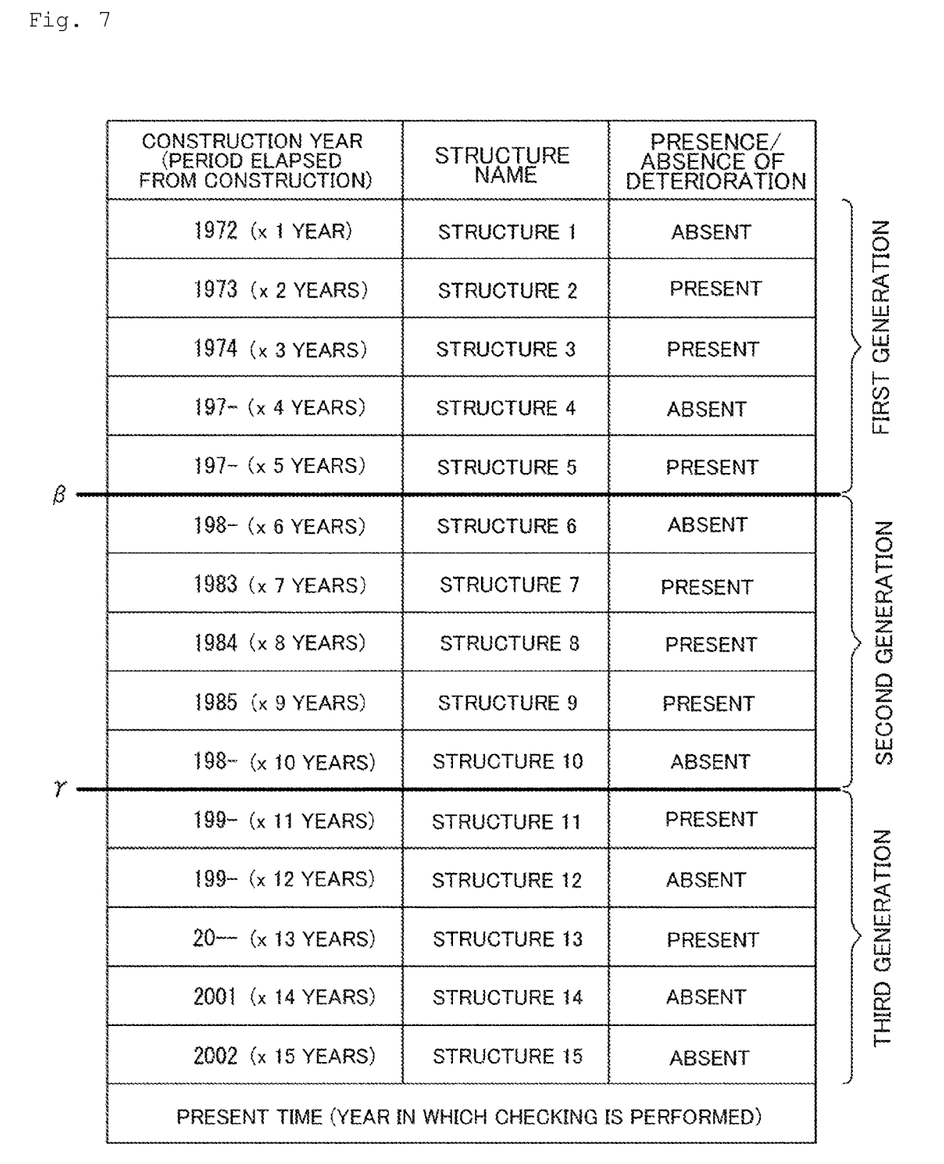
FIG. 7 is a diagram for illustrating an operation of a sorting unit illustrated in FIG. 1.

The sorting unit 23 compares the period x elapsed from the construction of the concrete structure shown in the checking result stored in the checking result holding unit 21 to the shortest period $\beta$ until appearance of the aging-induced deterioration/longest period $\gamma$ until appearance of the material-induced deterioration stored in the second holding unit 15 (Step S21). As illustrated in FIG. 7, it is assumed hereinafter that the shortest period $\beta$ until appearance of the aging-induced deterioration is a period between a period x5 elapsed from construction of a concrete structure having a structure name "5" and a period x6 elapsed from construction of a concrete structure having a structure name "6" (x6<x5). It is also assumed that the longest period $\gamma$ until appearance of the material-induced deterioration is a period between a period x10 elapsed from construction of a concrete structure having a structure name "10" and a period x11 elapsed from construction of a concrete structure having a structure name "11" (x11<x10).

When the period x elapsed from the construction of the concrete structure is not shorter than the shortest period $\beta$ until appearance of the aging-induced deterioration (x≥$\beta$), the sorting unit 23 sorts the concrete structure into the first generation, as illustrated in FIG. 7.

When the concrete structure is sorted into the first generation, the deterioration causing material presence/absence assessment unit 25 assesses, based on the deterioration presence/absence information, whether or not deterioration has occurred in the concrete structure (Step S22).

When assessing that no deterioration has occurred in the concrete structure (No in Step S22), the deterioration causing material presence/absence assessment unit 25 assesses that no deterioration causing material is used in the concrete structure (Step S23). When the concrete structure is sorted into the first generation and no deterioration has occurred in the concrete structure, neither the aging-induced deterioration nor the material-induced deterioration has occurred. Accordingly, the deterioration causing material presence/absence assessment unit 25 assesses that no deterioration causing material is used in the concrete structure.

When assessing that deterioration has occurred in the concrete structure (Yes in Step S22), the deterioration causing material presence/absence assessment unit 25 assesses that the presence or absence of a deterioration causing material used in the concrete structure is unknown (Step S24). The period x elapsed from the construction of the concrete structure sorted into the first generation is not shorter than the shortest period $\beta$ until appearance of the aging-induced deterioration. Accordingly, when deterioration occurs in the concrete structure, whether the deterioration is the deterioration due to the aging-induced deterioration cause or the deterioration due to the material-induced deterioration cause cannot be assessed. Therefore, the deterioration causing material presence/absence assessment unit 25 assesses that the presence or absence of a deterioration causing material used in the concrete structure is unknown.

When the period x elapsed from the construction of the concrete structure is shorter than the longest period $\gamma$ until appearance of the material-induced deterioration (x<$\gamma$), the sorting unit 23 sorts the concrete structure into the third generation, as illustrated in FIG. 7.

When the concrete structure is sorted into the third generation, the deterioration causing material presence/absence assessment unit 25 assesses that the presence or absence of a deterioration causing material used in the concrete structure is unknown (Step S24). When the concrete structure is sorted into the third generation, the period x elapsed from the construction of the concrete structure is shorter than the longest period $\gamma$ until appearance of the material-induced deterioration and therefore, even when a deterioration causing material is used, there is a possibility that deterioration due to the deterioration causing material has not appeared yet. Therefore, the deterioration causing material presence/absence assessment unit 25 assesses that the presence or absence of a deterioration causing material in the concrete structure is unknown.

When the period x elapsed from the construction of the concrete structure is not shorter than the longest period $\gamma$ until appearance of the material-induced deterioration and is shorter than the shortest period $\beta$ until appearance of the aging-induced deterioration (shorter than the first period), the sorting unit 23 sorts the concrete structure into the second generation, as illustrated n FIG. 7.

When the concrete structure is sorted into the second generation, the deterioration causing material presence/absence assessment unit 25 assesses, based on the deterioration presence/absence information, whether or not deterioration has occurred in the concrete structure (Step S25).

When assessing that no deterioration has occurred in the concrete structure (No in Step S25), the deterioration causing material presence/absence assessment unit 25 assesses that no deterioration causing material is used in the concrete structure (Step S23). When the concrete structure is sorted into the second generation and no deterioration has occurred in the concrete structure, it can be considered that no deterioration causing material is used since no deterioration has occurred even though the period x elapsed from the construction of the concrete structure has exceeded the longest period γ until appearance of the material-induced deterioration. Therefore, the deterioration causing material presence/absence assessment unit 25 assesses that no deterioration causing material is used in the concrete structure.

When assessing that deterioration has occurred in the concrete structure (Yes in Step S25), the deterioration causing material presence/absence assessment unit 25 assesses that a deterioration causing material is used in the concrete structure (Step S26). When the concrete structure is sorted into the second generation and deterioration has occurred in the concrete structure, it can be considered that, since the period x elapsed from the construction of the concrete structure has not exceeded the shortest period β until appearance of the aging-induced deterioration, the deterioration that has occurred in the concrete structure is not the deterioration due to the aging-induced deterioration cause, but the deterioration due to the material-induced deterioration cause. Therefore, the deterioration causing material presence/absence assessment unit 25 assesses that a deterioration causing material is used in the concrete structure.

Thus, in the assessment step, it is assessed that a deterioration causing material is used in the concrete structure having, in the checking result, deterioration and the period elapsed from the construction which is not shorter than the longest period (second period) until appearance of the material-induced deterioration and is shorter than the shortest period (first period) until appearance of the aging-induced deterioration.

Also, in the assessment step, it is assessed that no deterioration causing material is used in the concrete structure having no deterioration and having the period elapsed from the construction which is not shorter than the shortest period (first period) until appearance of the aging-induced deterioration. In the assessment step, it is further assessed that no deterioration causing material is used in the concrete structure having no deterioration and having the period elapsed from the construction which is not shorter than the longest period (second period) until appearance of the material-induced deterioration and is shorter than the shortest period (first period) until appearance of the aging-induced deterioration.

Figure 8:
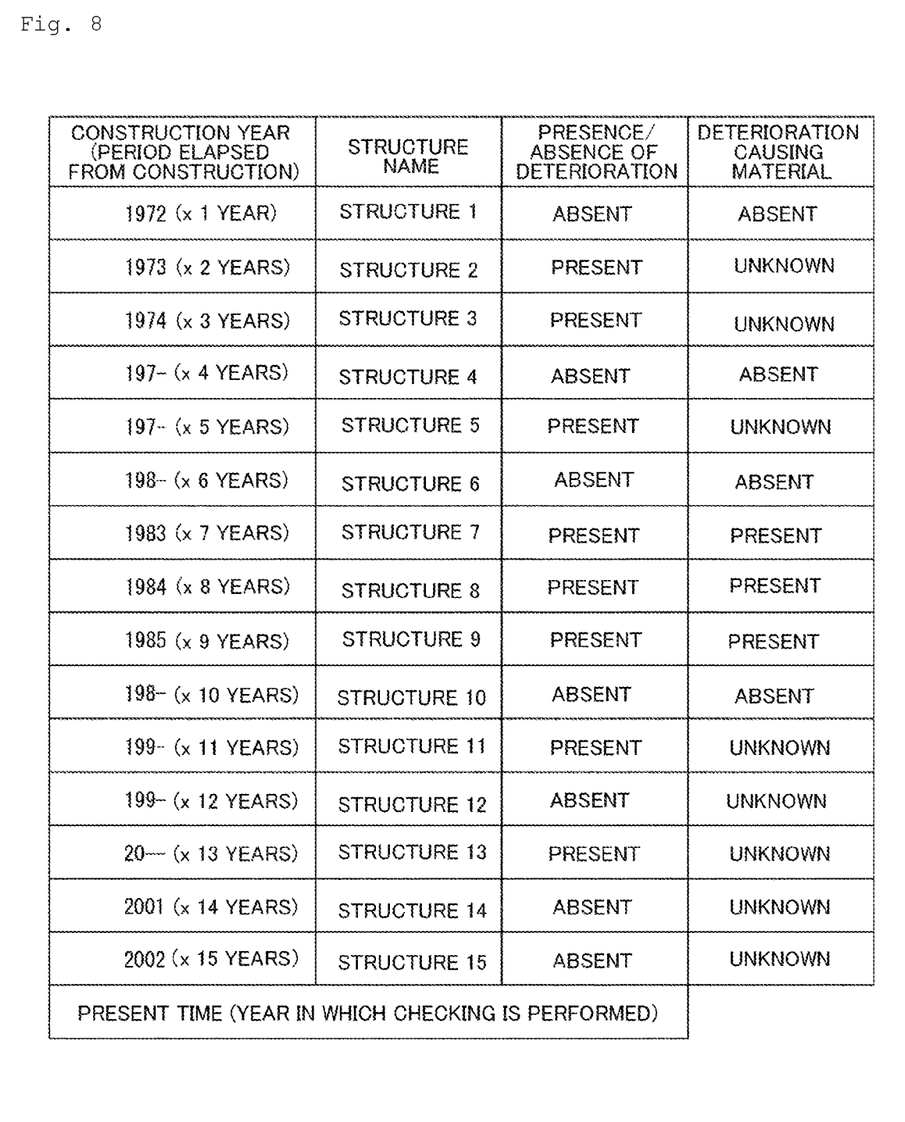
FIG. 8 is a diagram illustrating an example of an assessment result output from a deterioration causing material presence/absence assessment unit illustrated in FIG. 1.

When completing the assessment of the presence or absence of a deterioration causing material used in the concrete structure to be examined, the deterioration causing material presence/absence assessment unit 25 outputs a result of the assessment (Step S27). As illustrated in, e.g., FIG. 8, the deterioration causing material presence/absence assessment unit 25 adds, to the checking result stored in the checking result holding unit 21, the result of assessing the presence or absence of a deterioration causing material in use, and outputs the checking result with the assessment result.

Thus, in the present embodiment, the assessment device 1 includes the determination unit 10 and the assessment unit 20. The determination unit 10 determines the shortest period (first period) until appearance of the aging-induced deterioration, which corresponds to the shortest period until the deterioration of the concrete structure due to the aging-induced deterioration cause appears. The determination unit 10 also determines the longest period (second period) until appearance of the material-induced deterioration, which corresponds to the longest period until the deterioration of the concrete structure due to the material-induced deterioration cause appears. The assessment unit 20 assesses that a deterioration causing material is used in the concrete structure having, in the result of checking the concrete structure, deterioration and the period x elapsed from the construction which is not shorter than the longest period (second period) until appearance of the material-induced deterioration and is the shortest period (first period) until appearance of the aging-induced deterioration.

By using the period elapsed from the construction of the concrete structure and the shortest period until appearance of the aging-induced deterioration/longest period until appearance of the material-induced deterioration, it is possible to non-destructively assess the presence/absence of a deterioration causing material used in in the concrete structure. In the case of the deterioration due to the material-induced deterioration cause, even when simplified repair and maintenance is performed, there is a high possibility that deterioration such as cracking occurs every several years, since the deterioration causing material never disappears. Accordingly, it becomes possible to perform maintenance management considering safety and cost, such as execution of intensive checking or rebuilding, on the concrete structure using a deterioration causing material. Meanwhile, in the concrete structure using no deterioration causing material, even when checking intervals are elongated, problems are unlikely to occur until the deterioration due to the aging-induced deterioration cause appears. Accordingly, it is possible to reduce labor/cost required for checking. By thus non-destructively assessing the presence or absence of a deterioration causing material used in the concrete structure, it becomes possible to perform more efficient maintenance management of the concrete structure.

A computer can appropriately be used to function as the assessment device 1 described above, and such a computer can be implemented by storing, in a storage unit of the computer, a program describing details of processing for implementing a function (the individual steps described in the flow chart) of the assessment device 1 and causing a CPU of the computer to read the program and execute the program. This program can be recorded on a computer readable recording medium. The recording medium on which the program is recorded may also be a non-transient (non-transitory) recording medium. Alternatively, the program can also be provided via a network.

The present disclosure is not limited to the configuration specified in each of the embodiments described above, and various modifications can be made within a scope not departing from the gist of the invention described in claims. For example, it is possible to rearrange a function and the like included in each of components and the like without

REFERENCE SIGNS LIST

1 Assessment device
10 Determination unit
11 Deterioration cause/appearance period determination unit
12 First holding unit
13 First appearance period determination unit
14 Second appearance period determination unit
15 Second holding unit
20 Assessment unit
21 Checking result holding unit
22 Elapsed period extraction unit
23 Sorting unit
24 Deterioration presence/absence information extraction unit
25 Deterioration causing material presence/absence assessment unit

The invention claimed is:

1. A computer implemented method for assessing a presence of a deterioration causing material used in a concrete structure and causing deterioration therein, the method comprising:
determining a first period corresponding to a shortest period until deterioration of the concrete structure due to an aging-induced deterioration cause appears and a second period shorter than the first period and corresponding to a longest period until deterioration of the concrete structure due to a material-induced deterioration cause appears; and
assessing that the deterioration causing material is used in a concrete structure having, in a checking result indicating a period elapsed from construction of the concrete structure and presence of deterioration in the concrete structure, the deterioration and the period elapsed from the construction which is not shorter than the second period and is shorter than the first period.

2. The computer implemented method according to claim 1, wherein,
the assessing further comprises assessing the deterioration causing material is not used in both of a concrete structure having no deterioration and the period elapsed from the construction which is not shorter than the first period and a concrete structure having no deterioration and the period elapsed from the construction which is not shorter than the second period and is shorter than the first period.

3. The assessment method according to claim 1, wherein, the determining further comprises:
for each of a plurality of the aging-induced deterioration causes, predicting a period until deterioration of the concrete structure due to the deterioration cause appears;
determining the shortest one of the periods predicted for the plurality of individual aging-induced deterioration causes as the first period;
for each of a plurality of the material-induced deterioration causes, predicting a period until deterioration of the concrete structure due to the deterioration cause appears is predicted; and
determining the longest one of the periods predicted for the plurality of individual material-caused deterioration causes as the second period.

4. An assessment device for assessing the presence or absence of a deterioration causing material used in a concrete structure and causing deterioration therein, the device comprising a processor configured to execute a method comprising:
determining a first period corresponding to a shortest period until deterioration of the concrete structure due to an aging-induced deterioration cause appears and a second period shorter than the first period and corresponding to a longest period until deterioration of the concrete structure due to a material-induced deterioration cause appears; and
assessing that the deterioration causing material is used in a concrete structure having, in a checking result indicating a period elapsed from construction of the concrete structure and presence of deterioration in the concrete structure, the deterioration and the period elapsed from the construction which is not shorter than the second period and is shorter than the first period.

5. A computer-readable non-transitory recording medium storing computer-executable program instructions that when executed by a processor cause a computer to execute a method comprising:
determining a first period corresponding to a shortest period until deterioration of the concrete structure due to an aging-induced deterioration cause appears and a second period shorter than the first period and corresponding to a longest period until deterioration of the concrete structure due to a material-induced deterioration cause appears; and
assessing that the deterioration causing material is used in a concrete structure having, in a checking result indicating a period elapsed from construction of the concrete structure and presence of deterioration in the concrete structure, the deterioration and the period elapsed from the construction which is not shorter than the second period and is shorter than the first period.

6. The computer implemented method according to claim 1, wherein the deterioration includes a crack.

7. The computer implemented method according to claim 1, wherein the deterioration causing material used in the concrete structure is represented by a ratio of sea sand in use.

8. The computer implemented method according to claim 2, wherein, the determining further comprises:
for each of a plurality of the aging-induced deterioration causes, predicting a period until deterioration of the concrete structure due to the deterioration cause appears;
determining the shortest one of the periods predicted for the plurality of individual aging-induced deterioration causes as the first period;
for each of a plurality of the material-induced deterioration causes, predicting a period until deterioration of the concrete structure due to the deterioration cause appears is predicted; and
determining the longest one of the periods predicted for the plurality of individual material-caused deterioration causes as the second period.

9. The assessment device according to claim 4, wherein wherein, the assessing further comprises assessing the deterioration causing material is not used in both of a concrete structure having no deterioration and the period elapsed from the construction which is not shorter than the first period and a concrete structure having no deterioration and the period elapsed from the construction which is not shorter than the second period and is shorter than the first period.

10. The assessment device according to claim 4, wherein the determining further comprises:
- for each of a plurality of the aging-induced deterioration causes, predicting a period until deterioration of the concrete structure due to the deterioration cause appears;
- determining the shortest one of the periods predicted for the plurality of individual aging-induced deterioration causes as the first period;
- for each of a plurality of the material-induced deterioration causes, predicting a period until deterioration of the concrete structure due to the deterioration cause appears is predicted; and
- determining the longest one of the periods predicted for the plurality of individual material-caused deterioration causes as the second period.

11. The assessment device according to claim 4, wherein the deterioration includes a crack.

12. The assessment device according to claim 4, wherein the deterioration causing material used in the concrete structure is represented by a ratio of sea sand in use.

13. The assessment device according to claim 9, wherein the determining further comprises:
- for each of a plurality of the aging-induced deterioration causes, predicting a period until deterioration of the concrete structure due to the deterioration cause appears;
- determining the shortest one of the periods predicted for the plurality of individual aging-induced deterioration causes as the first period;
- for each of a plurality of the material-induced deterioration causes, predicting a period until deterioration of the concrete structure due to the deterioration cause appears is predicted; and
- determining the longest one of the periods predicted for the plurality of individual material-caused deterioration causes as the second period.

14. The computer-readable non-transitory recording medium according to claim 5, wherein, the assessing further comprises assessing the deterioration causing material is not used in both of a concrete structure having no deterioration and the period elapsed from the construction which is not shorter than the first period and a concrete structure having no deterioration and the period elapsed from the construction which is not shorter than the second period and is shorter than the first period.

15. The computer-readable non-transitory recording medium according to claim 5, wherein the determining further comprises:
- for each of a plurality of the aging-induced deterioration causes, predicting a period until deterioration of the concrete structure due to the deterioration cause appears;
- determining the shortest one of the periods predicted for the plurality of individual aging-induced deterioration causes as the first period;
- for each of a plurality of the material-induced deterioration causes, predicting a period until deterioration of the concrete structure due to the deterioration cause appears is predicted; and
- determining the longest one of the periods predicted for the plurality of individual material-caused deterioration causes as the second period.

16. The computer-readable non-transitory recording medium according to claim 5, wherein the deterioration includes a crack.

17. The computer-readable non-transitory recording medium according to claim 5, wherein the deterioration causing material used in the concrete structure is represented by a ratio of sea sand in use.

18. The computer-readable non-transitory recording medium according to claim 14, wherein the determining further comprises:
- for each of a plurality of the aging-induced deterioration causes, predicting a period until deterioration of the concrete structure due to the deterioration cause appears;
- determining the shortest one of the periods predicted for the plurality of individual aging-induced deterioration causes as the first period;
- for each of a plurality of the material-induced deterioration causes, predicting a period until deterioration of the concrete structure due to the deterioration cause appears is predicted; and
- determining the longest one of the periods predicted for the plurality of individual material-caused deterioration causes as the second period.

* * * * *